United States Patent [19]

Heeres et al.

[11] Patent Number: 4,598,085

[45] Date of Patent: Jul. 1, 1986

[54] FUNGICIDAL 1-(2-ARYL-2-R-ETHYL)-1H-1,2,4-TRIAZOLES

[75] Inventors: Jan Heeres, Vosselaar; Leo J. J. Backx, Arendonk; Joseph A. Mostmans, Antwerp, all of Belgium

[73] Assignee: Janssen Pharmaceutica N.V., Beerse, Belgium

[21] Appl. No.: 341,424

[22] Filed: Jan. 21, 1982

Related U.S. Application Data

[63] Continuation of Ser. No. 791,632, Apr. 27, 1977, abandoned, which is a continuation-in-part of Ser. No. 713,308, Aug. 10, 1976, abandoned.

[51] Int. Cl.$^4$ .................. A01N 43/653; C07D 249/08
[52] U.S. Cl. ........................................ 514/383; 71/76; 71/92; 548/262; 560/62; 560/102; 560/103; 560/104; 568/642; 568/656; 568/660; 568/807; 568/808; 568/812
[58] Field of Search ................. 424/269; 548/262; 514/383

[56] References Cited

U.S. PATENT DOCUMENTS

| 3,647,814 | 3/1972 | Greenfield | 548/262 |
| 3,658,813 | 4/1972 | Godefroi et al. | 548/341 |
| 3,717,655 | 2/1973 | Godefroi et al. | 548/341 |
| 3,821,394 | 6/1974 | Timmler et al. | 424/273 |
| 3,897,438 | 7/1975 | Draber et al. | 424/263 |
| 3,927,017 | 12/1975 | Heeres et al. | 548/335 |
| 3,991,201 | 11/1976 | Heeres et al. | 424/273 |
| 4,005,083 | 1/1977 | Buchel et al. | 548/101 |
| 4,115,578 | 9/1978 | Miller et al. | 548/101 |
| 4,315,016 | 2/1982 | Balasubramanyan et al. | 548/262 |
| 4,327,104 | 4/1982 | Timmler et al. | 548/262 |

OTHER PUBLICATIONS

Ainsworth et al., J. Med. Chem., vol. 5, pp. 383–389 (1962).

Primary Examiner—Alton D. Rollins
Attorney, Agent, or Firm—Geoffrey G. Dellenbaugh

[57] ABSTRACT

Novel compounds of the class of 1-(2-aryl-2-R-ethyl)-1H-1,2,4-triazoles having fungicidal and plant-growth regulating properties.

43 Claims, No Drawings

FUNGICIDAL 1-(2-ARYL-2-R-ETHYL)-1H-1,2,4-TRIAZOLES

CROSS-REFERENCE TO RELATED APPLICATIONS

This is a continuation of application Ser. No. 791,632 filed Apr. 27, 1977, now abandoned, which in turn is a continuation-in-part of application Ser. No. 713,308, filed Aug. 10, 1976, now abandoned.

BACKGROUND OF THE INVENTION

The invention pertains to the field of 1-(2-aryl-2-R-ethyl)-1H-1,2,4-triazoles which demonstrate fungicidal and plant-growth regulating properties. In the prior art there may be found a number of fungicidal and plant-growth regulating imidazole and triazole derivatives. The compounds of this invention differ from the known triazole derivatives by the nature of the substituted ethyl side chain present in the 1-position of the triazole nucleus and from the imidazole derivatives essentially by the replacement of the imidazole group with a 1H-1,2,4-triazole group.

The prior art may be represented by the following references:

U.S. Pat. No. 3,717,655;
U.S. Pat. No. 3,658,813;
U.S. Pat. No. 3,927,017;
U.S. Pat. No. 3,821,394;
U.S. Pat. No. 3,897,438; and
U.S. Pat. No. 3,647,814.

DESCRIPTION OF THE PREFERRED EMBODIMENTS

The novel 1-(2-aryl-2-R-ethyl)-1H-1,2,4-triazoles with which this invention is concerned may structurally be represented by the formula:

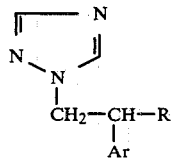

(I)

wherein:
Ar is a member selected from the group consisting of phenyl, mono-, di- and tri-halophenyl, lower alkylphenyl, lower alkyloxyphenyl, nitrophenyl, cyanophenyl and trifluoromethylphenyl; and
R is a member selected from the group consisting of alkyl having from 1 to 10 carbon atoms, cycloalkyl, cycloalkyl-lower alkyl, lower alkenyl, aryl-lower alkyl, aryloxy-lower alkyl and a radical of the formula —O—$R^1$, wherein $R^1$ is selected from the group consisting of alkyl having from 1 to 10 carbon atoms, lower alkenyl, lower alkynyl and aryl-lower alkyl, said aryl being selected from the group consisting of phenyl, naphthalenyl and substituted phenyl, wherein said substituted phenyl is phenyl having from 1 to 3 substituents independently selected from the group consisting of halo, lower alkyl, lower alkyloxy, cyano, nitro and phenyl, provided that when more than one substituents are present only one thereof may be selected from the group consisting of cyano, nitro and phenyl.

The term "alkyl" as used in the definition of R and $R^1$ is meant to include straight and branch chained aliphatic hydrocarbon radicals containing from 1 to 10 carbons, such as, for example, methyl, ethyl, 1-methylethyl, 1,1-dimethylethyl, propyl, 1-methylpropyl, 2-methylpropyl, butyl, pentyl, hexyl, heptyl, octyl, decyl and the like; "lower alkyl" as used herein, refers to straight or branch chained alkyl radicals containing from 1 to about 6 carbon atoms, such as, for example, methyl, ethyl, 1-methylethyl, propyl, 1-methylpropyl, 2-methylpropyl, butyl, pentyl, hexyl and the like; "lower alkenyl" refers to straight and branch chained unsaturated alkenyl radicals having from 3 to 6 carbon atoms, such as, for example, 2-propenyl, 1-methyl-2-propenyl, 2-butenyl, 3-butenyl, 2-hexenyl and the like; the term "cycloalkyl" refers to cyclic hydrocarbon radicals having from 3 to 6 carbon atoms, such as cyclopropyl, cyclobutyl, cyclopentyl and cyclohexyl; and the term "halo" is generic to halogens of atomic weight less than 127, i.e., chloro, bromo, fluoro and iodo.

The physiologically acceptable acid addition salts of the foregoing compounds (I) are also embraced within the scope of this invention.

One preferred group of compounds within the scope of formula (I) may be represented by the formula:

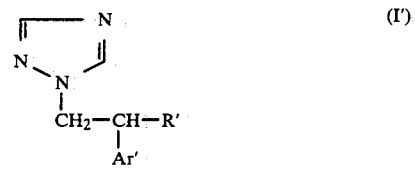

(I')

wherein
Ar' is selected from the group consisting of phenyl, mono- and di-halophenyl, and methylphenyl; and
R' is selected from the group consisting of alkyl having from 1 to 10 carbon atoms, cycloalkyl, lower alkenyl, arylmethyl and arylethyl, wherein said aryl is preferably phenyl, halophenyl, methylphenyl or methoxyphenyl.

Especially preferred within the scope of formula (I') are compounds wherein Ar' is phenyl, chlorophenyl, fluorophenyl, bromophenyl, dichlorophenyl, dibromophenyl or methylphenyl, the most preferred being dichloro- and dibromophenyl; and, wherein R' is alkyl having from 1 to 8 carbon atoms, cycloalkyl, or 2-propenyl, the most preferred being alkyl having from 1 to 6 carbon atoms and 2-propenyl.

Typical examples of preferred compounds within the scope of formula (I') are the following:
1-[2-(2,4-dichlorophenyl)propyl]-1H-1,2,4-triazole;
1-[2-(2,4-dichlorophenyl)butyl]-1H-1,2,4-triazole;
1-[2-(2,4-dichlorophenyl)phenyl]-1H-1,2,4-triazole;
1-[2-(2,4-dichlorophenyl)-3-methylbutyl]-1H-1,2,4-triazole;
1-[2-(2,4-dichlorophenyl)-4-pentenyl]-1H-1,2,4-triazole;
1-[2-(2,4-dichlorophenyl)hexyl]-1H-1,2,4-triazole;
1-[2-(2,4-dichlorophenyl)-4-methylpentyl]-1H-1,2,4-triazole;
1-[2-(2,4-dichlorophenyl)-3-methylpentyl]-1H-1,2,4-triazole;
1-[2-(2,4-dichlorophenyl)heptyl]-1H-1,2,4-triazole;
1-[2-cyclopentyl-2-(2,4-dichlorophenyl)ethyl]-1H-1,2,4-triazole;

1-[2-cyclohexyl-2-(2,4-dichlorophenyl)ethyl]-1H-1,2,4-triazole;

1-[3-(4-chlorophenyl)-2-(2,4-dichlorophenyl)propyl]-1H-1,2,4-triazole;

1-[2-(2,4-dibromophenyl)hexyl]-1H-1,2,4-triazole;

1-[2-(2,4-dibromophenyl)-4-methylpentyl]-1H-1,2,4-triazole;

1-[2-(2,4-dibromophenyl)-3-methylbutyl]-1H-1,2,4-triazole;

1-[2-(2,4-dibromophenyl)-3-methylpentyl]-1H-1,2,4-triazole;

1-[2-(4-fluorophenyl)-4-(4-methylphenyl)butyl]-1H-1,2,4-triazole; and

1-[4-(4-chlorophenyl)-2-(4-fluorophenyl)butyl]-1H-1,2,4-triazole.

Another preferred group of compounds of formula (I) are represented by the formula:

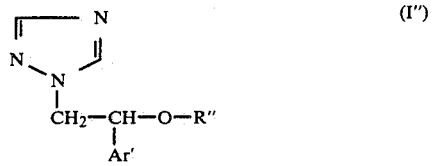

wherein Ar' is as defined above and R" is selected from the group consisting of alkyl having from 1 to 10 carbon atoms, lower alkenyl and lower alkynyl.

Especially preferred compounds within the scope of formula (I") are those wherein Ar' is phenyl, chlorophenyl, fluorophenyl, bromophenyl, dichlorophenyl, dibromophenyl or methylphenyl; the most preferred being dichloro- and dibromophenyl; and, wherein R" is alkyl having from 1 to 8 carbon atoms, 2-propenyl or 2-propynyl, the most preferred alkyls having from 1 to 6 carbon atoms.

Typical preferred compounds of formula (I") are, for example, the following:

1-[2-(2,4-dichlorophenyl)-2-ethoxyethyl]-1H-1,2,4-triazole;

1-[2-(2,4-dichlorophenyl)-2-propoxyethyl]-1H-1,2,4-triazole;

1-[2-(2,4-dichlorophenyl)-2-(2-propenyloxy)ethyl]-1H-1,2,4-triazole;

1-[2-butoxy-2-(2,4-dichlorophenyl)ethyl]-1H-1,2,4-triazole;

1-[2-(2,4-dichlorophenyl)-2-(pentyloxy)ethyl]-1H-1,2,4-triazole;

1-[2-(2,4-dichlorophenyl)-2-(hexyloxy)ethyl]-1H-1,2,4-triazole;

1-[2-(2,4-dichlorophenyl)-2-(heptyloxy)ethyl]-1H-1,2,4-triazole; and

1-[2-(2,4-dichlorophenyl)-2-(2-methylpropoxy)ethyl]-1H-1,2,4-triazole.

The compounds of formula (I) which may be represented by the formula:

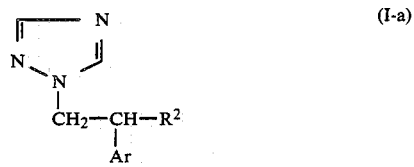

wherein Ar is a previously defined and $R^2$ is selected from the group consisting of alkyl, cycloalkyl, cycloalkyl-lower alkyl, lower alkenyl, aryl-lower alkyl and aryloxy-lower alkyl, may conveniently to prepared by N-alkylating 1H-1,2,4-triazole (II) with an appropriate reactive ester of formula (III) wherein Ar and $R^2$ are as previously defined and X is a reactive ester function such as, for example, halo, methanesulfonyl, 4-methylbenzenesulfonyl and the like.

In carrying out the reaction of (II) and (III) it is appropriate to first convert (II) into an alkali metal salt, preferably the sodium salt, by the reaction of (II) with an appropriate strong metal base, such as, for example, sodium hydride, sodium methanolate, sodium amide and the like and thereafter stirring and heating said metal salt with (III) in an appropriate polar organic solvent. Suitable solvents for this purpose include amides such as, for example, N,N-dimethylformamide and N,N-dimethylacetamide, and nitriles such as, for example acetonitrile, benzonitrile and the like.

Alternatively (II) and (III) may be reacted directly with each other without previous salt formation, in which case the reaction is preferably carried out in an appropriate polar organic solvent as defined hereabove, in the presence of an appropriate base to pick up the acid which is liberated during the course of the reaction. Suitable bases which may advantageously be employed include inorganic bases such as, for example, sodium and potassium carbonate and hydrogen carbonate and the like, and organic bases such as, for example, N,N-diethylethanamine, pyridine and the like. Somewhat elevated temperatures are appropriate to enhance the rate of the reaction and most preferably the reaction is carried out at the reflux temperature of the reaction mixture.

The foregoing reactions may be illustrated as follows:

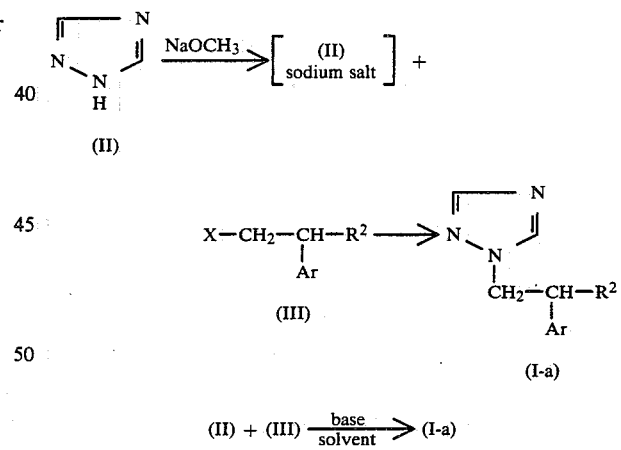

The compounds of formula (I) which are represented by the formula:

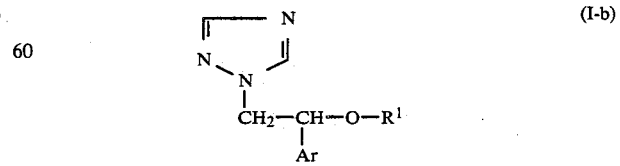

wherein Ar and $R^1$ are as previously defined may be prepared by O-alkylating a hydroxy compound of the formula (IV) with an appropriate reactive ester of formula $XR^1$ wherein $R^1$ and $X$ are as previously defined following standard procedures of O-alkylation. In a preferred method of carrying out said O-alkylation reaction the hydroxycompound (IV) is first converted into an alkali metal salt thereof of treating (IV) with an appropriate metallating agent such as, for example, sodium hydride, sodium methanolate, sodium amide and the like whereafter the resulting metal salt is reacted with $XR^1$. Said reaction is carried out in an appropriate reaction-inert organic solvent such as, for example, an aromatic hydrocarbon, e.g. benzene, methylbenzene and the like; a ketone, e.g., 2-propanone, 4-methyl-2-pentanone and the like; an ether, e.g., 1,1′-oxybisethane, 2,2′-oxybispropane and the like; an amide, e.g., N,N-dimethylformamide, N,N-dimethylacetamide; or another common solvent such as, for example, dimethylsulfoxide, nitrobenzene and the like; or in a mixture of such solvents.

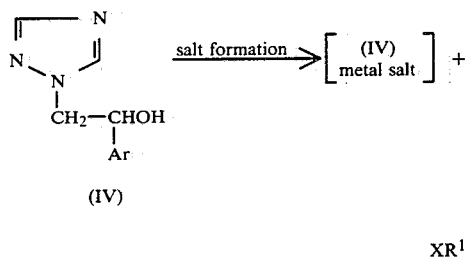

It is evident that the compounds of formula (I) obtained following the procedures described herebefore are isolated from the reaction mixture and, if necessary, further purified by the application of methodologies known in the art.

The compounds of formula (I), obtained in base form in the foregoing procedures, may be converted to their physiologically acceptable acid addition salts by the reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the reactive ester intermediates of formula (III) are known compounds and they may all be prepared according to art-known procedures as described in the literature for the preparation of those known compounds. Such compounds and methods of preparing the same are described, for example, in U.S. Pat. No. 3,927,017.

In general said intermediates of formula (III) are prepared by converting the corresponding alcohol (V) into the desired reactive ester according to methodologies generally known in the art. For example, methanesulfonates and 4-methylbenzenesulfonates are easily obtained by treating the alcohol with methanesulfonyl chloride or 4-methylbenzenesulfonyl chloride respectively, in the presence of an appropriate acid acceptor, such as, for example, pyridine. Halides may be obtained by treating the alcohol with an appropriate halogenating agent, such as, for example, phosphor pentachloride, phosphorous tribromide, etc.

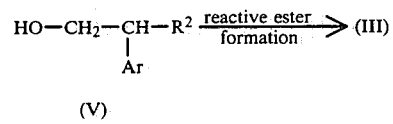

The intermediate alcohols of formula (V), a number of which are known compounds, may be prepared according to known procedures, such as, for example, the following:

An appropriately substituted arylacetonitrile of formula (VI) is alkylated with an appropriate reactive ester $R^2X$, (VII). Said alkylation reaction is preferably carried out by contacting first the arylacetonitrile with an appropriate strong base, such as, for example, sodium hydride, and thereafter adding the reactive ester to the reaction mixture. Suitable solvents for this reaction include amides such as N,N-dimethylformamide, N,N-dimethylacetamide and hexamethylphosphoric triamide, other common polar solvents such as dimethylsulfoxide, or mixtures of such solvents with, for example, an aromatic hydrocarbon, such as, benzene.

The substituted arylacetonitrile (VIII) obtained in the foregoing step is then converted into an alkyl ester (IX) of the corresponding carboxylic acid. This nitrile-to-ester conversion may be achieved in one step, for example, by heating the nitrile in an appropriate alcohol, or a mixture of an alcohol with an appropriate reaction-inert organic solvent, such as, 2,2′-oxybispropane, in the presence of a strong non-oxidizing mineral acid such as, for example, hydrochloric acid. Alternatively the nitrile may be first hydrolyzed to the corresponding arylacetic acid in the usual manner, e.g., with sodium hydroxide in 1,2-ethanediol, and said acid may thereafter be converted into the desired ester thereof by classical means.

The esters (IX) may also be obtained by alkylating an appropriate alkyl arylacetate (X) with $R^2X$ according to known procedures.

The alcohols (V) are then obtained after reduction of (IX) with an appropriate reducing agent such as, for example, lithium aluminium hydride, lithium borohydride, or sodium borohydride in the presence of a lithium salt, preferably a halide such as, lithium iodide or lithium chloride.

The foregoing reactions are illustrated in the following schematic representation:

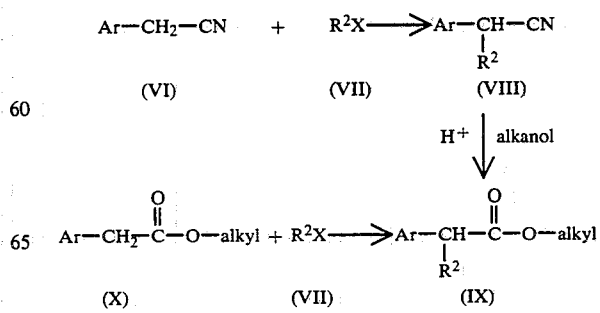

(IX) 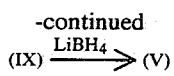 (V)

The starting materials of formula (VI) and (VII) herein are generally known and may be prepared following art-known procedures. For example, starting materials of formula (VII) wherein $R^2$ stands for aryloxy-lower alkyl and X stands for halo, are easily prepared by O-alkylating an appropriate hydroxyarene with an appropriate dihalo-lower alkane using, for example, aqueous alkali as a reaction medium.

Intermediates of formula (IV) and a method of preparing them are described in Ger. O.L.S. No. 24.31.407. According to said reference the intermediates (IV) may be derived from the corresponding ketones (XI) by reducing the latter with an appropriate reducing agent such as, for example, aluminium 2-propanolate, complex hydrides such as, sodium borohydride or by catalytic hydrogenation using an appropriate catalyst such as, for example, Raney-nickel.

An other and novel method of preparing the intermediates of formula (IV) is by the reaction of 1H-1,2,4-triazole (II) with an appropriate reactive ester of formula (XII) wherein X is a reactive ester group as previously defined, following similar procedures as described hereinabove for the preparation of the compounds (I) starting from (II) and (III).

The foregoing reactions are illustrated in the following schematic representation:

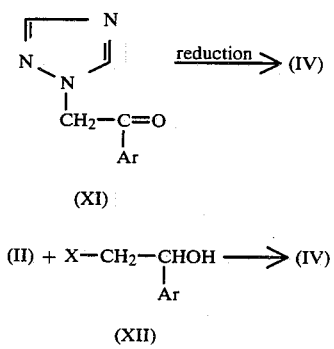

The ultimate starting materials in each of the foregoing procedures are generally known and they may all be prepared following art-known procedures.

Due to the presence of an asymmetric carbon in the subject compounds (I), it is evident that their existence in the form of stereochemical optical isomers (enantiomers) is possible. If desired, the resolution and isolation or the production of a particular form can be accomplished by application of the general principles known in the art. Said enantiomers are naturally intended to be included within the scope of this invention.

The compounds of formula (I) and the acid addition salts thereof are useful agents in combatting fungi. They are especially useful as potent agricultural fungicides, being active against a wide variety of fungi such as, for example, those responsible for the occurrence of powdery mildew on different plant species, e.g., *Erysiphe graminis, Erysiphe polygoni, Erysiphe cichoracearum, Erysiphe polyphaga, Podosphaera leucotrichia, Sphaerotheca pannosa, Sphaerotheca mors-uvae* and *Uncinulla necator;* and against other phytopathogenic fungi such as, for example, *Septoria apii* and *Uromyces phaseoli.*

The useful antifungal properties of the compounds of this invention are more clearly illustrated by the results obtained in the following experiments. The compounds for which experimental data are presented hereafter are not given for the purpose of limiting the invention thereto but only to exemplify the useful antifungal properties of all the compounds within the scope of formula (I).

A. Prophylactic activity against *Erysiphe cichoracearum* on gherkins upon foliar treatment.

Young gherkin plants, about 10 days old, were sprayed with an aqueous solution containing 100, 10 or 1 ppm. (parts per million) of the compound to be tested, while controls were kept untreated. After drying of the plants, artificial infection with spores of *Erysiphe cichoracearum* was carried out by slightly rubbing the plants with a heavily infected leaf. At the 15th day after artificial infection the degree of fungal attack was evaluated by estimating the percent of leaf surface attacked by the fungus. Three plants were used per object and mean values were calculated for these 3 plants. The results are presented in Tables I and II according to the following score system:

| score | % of leaf surface attacked |
|-------|----------------------------|
| 0     | 0                          |
| 1     | ≦10                        |
| 2     | 11 to 50                   |
| 3     | >50                        |

TABLE I

Prophylactic activity against *Erysiphe cichoracearum* on gherkins (foliar treatment).

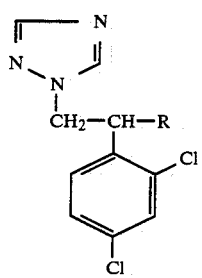

| Compound no. | R | Base or Salt | Scores 100 ppm. | 10 ppm. | 1 ppm. |
|---|---|---|---|---|---|
| 1 | CH$_3$ | base | 0 | 0 | 0 |

TABLE I-continued

Prophylactic activity against *Erysiphe cichoracearum* on gherkins (foliar treatment).

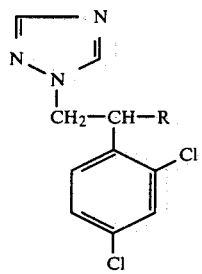

| Compound no. | R | Base or Salt | Scores 100 ppm. | 10 ppm. | 1 ppm. |
|---|---|---|---|---|---|
| 2 | C$_2$H$_5$ | base | 0 | 0 | 0 |
| 3 | nC$_3$H$_7$ | base | 0 | 0 | 0 |
| 4 | iC$_3$H$_7$ | HNO$_3$ | 0 | 0 | 0 |
| 5 | nC$_4$H$_9$ | HNO$_3$ | 0 | 0 | 0 |
| 6 | CH$_2$—CH(CH$_3$)$_2$ | HNO$_3$ | 0 | 0 | 0 |
| 7 | CH(CH$_3$)—CH$_2$—CH$_3$ | HNO$_3$ | 0 | 0 | 0 |
| 8 | nC$_8$H$_{17}$ | HNO$_3$ | 0 | 0 | 2 |
| 9 | CH$_2$—CH=CH$_2$ | HNO$_3$ | 0 | 0 | 0 |
| 10 | cyclopentyl | HNO$_3$ | 0 | 0 | 1 |
| 11 | cyclohexyl | base | 0 | 1 | 2 |
| 12 | (CH$_2$)$_2$-cyclopentyl | base | 0 | 1 | 2 |
| 13 | CH$_2$-cyclohexyl | HNO$_3$.0.5H$_2$O | 1 | 3 | 3 |
| 14 | (CH$_2$)$_2$-cyclohexyl | base | 0 | 0 | 2 |
| 15 | CH$_2$—(4-Cl—C$_6$H$_4$) | HNO$_3$ | 0 | 0 | 3 |
| 16 | CH$_2$—(2-Br—C$_6$H$_4$) | HNO$_3$ | 0 | 0 | 0 |
| 17 | CH$_2$—(4-C$_6$H$_5$—C$_6$H$_4$) | HCl | 0 | 0 | 2 |
| 18 | (CH$_2$)$_2$—O—(4-Br—C$_6$H$_4$) | HNO$_3$ | 0 | 0 | 3 |
| 19 | (CH$_2$)$_3$—O—(3,5-Cl$_2$—C$_6$H$_3$) | HNO$_3$ | 1 | 2 | 3 |
| 20 | (CH$_2$)$_3$—O—(3-CH$_3$—4-Cl—C$_6$H$_3$) | HNO$_3$ | 1 | 3 | 3 |
| 21 | (CH$_2$)$_3$—O—(2-CH$_3$—4-Cl—C$_6$H$_3$) | HNO$_3$ | 1 | 0 | 2 |
| 22 | (CH$_2$)$_3$—O—(2-Br—4-CH$_3$—C$_6$H$_3$) | HNO$_3$ | 0 | 0 | 1 |
| 23 | (CH$_2$)$_3$—O—(2,4-Cl$_2$—6-CH$_3$—C$_6$H$_2$) | HNO$_3$ | 2 | 2 | 3 |
| 24 | (CH$_2$)$_3$—O—(2,4,6-Br$_3$—C$_6$H$_2$) | HNO$_3$ | 0 | 0 | 1 |
| 25 | (CH$_2$)$_3$—O—(2-Cl—4-C$_6$H$_5$—C$_6$H$_3$) | HNO$_3$ | 0 | 1 | 2 |
| 26 | (CH$_2$)$_3$—O—(2-naphthalenyl) | HNO$_3$ | 0 | 0 | 2 |
| 27 | O—CH$_3$ | HNO$_3$ | 0 | 0 | 3 |
| 28 | O—C$_2$H$_5$ | HNO$_3$ | 0 | 0 | 0 |
| 29 | O—nC$_3$H$_7$ | HNO$_3$ | 0 | 0 | 0 |
| 30 | O—nC$_4$H$_9$ | HNO$_3$ | 0 | 0 | 0 |
| 31 | O—nC$_5$H$_{11}$ | HNO$_3$ | 0 | 0 | 1 |
| 32 | O—nC$_6$H$_{13}$ | HNO$_3$ | 0 | 0 | 0 |
| 33 | O—nC$_7$H$_{15}$ | HNO$_3$ | 0 | 0 | 1 |
| 34 | O—CH$_2$—CH=CH$_2$ | HNO$_3$ | 0 | 0 | 0 |
| 35 | O—CH$_2$—C≡CH | base | 0 | 0 | 2 |

TABLE II

Prophylactic activity against *Erysiphe cichoracearum* on gherkins (foliar treatment).

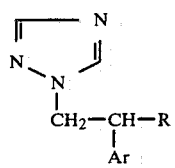

| Compound no. | Ar | R | Base or Salt | Scores 100 ppm. | 10 ppm. | 1 ppm. |
|---|---|---|---|---|---|---|
| 36 | 2,4-Br$_2$—C$_6$H$_3$ | nC$_4$H$_9$ | HNO$_3$ | 0 | 0 | 0 |
| 37 | 2-Cl—C$_6$H$_4$ | (CH$_2$)$_2$—(4-Br—C$_6$H$_4$) | HCl | 0 | 1 | 2 |
| 38 | 4-Cl—C$_6$H$_4$ | (CH$_2$)$_2$—(4-Cl—C$_6$H$_4$) | HCl | 0 | 1 | 2 |
| 39 | 4-Br—C$_6$H$_4$ | (CH$_2$)$_2$—(4-Cl—C$_6$H$_4$) | base | 0 | 2 | 3 |
| 40 | 4-Br—C$_6$H$_4$ | (CH$_2$)$_2$—(2-OCH$_3$—C$_6$H$_4$) | HCl | 0 | 1 | 2 |
| 41 | 4-Br—C$_6$H$_4$ | (CH$_2$)$_2$—(4-Br—C$_6$H$_4$) | HCl | 0 | 3 | 3 |
| 42 | 4-F—C$_6$H$_4$ | (CH$_2$)$_2$—(4-Cl—C$_6$H$_4$) | HCl | — | 0 | 1 |
| 43 | 4-F—C$_6$H$_4$ | (CH$_2$)$_2$—(4-CH$_3$—C$_6$H$_4$) | HCl | 0 | 0 | 1 |
| 44 | 4-CH$_3$—C$_6$H$_4$ | (CH$_2$)$_2$—(4-Cl—C$_6$H$_4$) | HCl | 0 | 2 | 3 |

B. Prophylactic action against *Erysiphe graminis* on barley upon foliar treatment.

Young barley plants, about 8 cm. high, were sprayed with an aqueous solution containing 100, 10 or 1 ppm. of the compound under investigation while controls were kept untreated. After drying of the plants they are artificially infected by dusting them with conidia of *Erysiphe graminis*. Fungal attack was evaluated 10 days thereafter in the same manner as described in experiment A. The results of this experiment are represented in Table III wherein the compound numbers and the score system are the same as in Tables I and II.

TABLE III

Prophylactic action against *Erysiphe graminis* on barley upon foliar treatment.

| Compound no. | 100 ppm. | 10 ppm. | 1 ppm. |
|---|---|---|---|
| 1 | 1 | 1 | 3 |
| 2 | 0 | 0 | 2 |
| 3 | 0 | 1 | 2 |
| 4 | 0 | 1 | 2 |
| 5 | 0 | 1 | 2 |
| 6 | 0 | 0 | 1 |
| 7 | 0 | 1 | 1 |
| 8 | 0 | 1 | 2 |
| 9 | 0 | 1 | 3 |
| 10 | 0 | 1 | 2 |
| 11 | 1 | 2 | 2 |
| 12 | 1 | 3 | 3 |
| 13 | 0 | 0 | 1 |
| 14 | 1 | 3 | 3 |
| 15 | 0 | 1 | 1 |
| 16 | 1 | 2 | 3 |
| 17 | 1 | 2 | 3 |
| 18 | 1 | 2 | 3 |
| 19 | 1 | 3 | 3 |
| 22 | 1 | 2 | 3 |
| 24 | 1 | 3 | 3 |
| 26 | 2 | 2 | 3 |
| 27 | 2 | 3 | 3 |
| 28 | 1 | 1 | 2 |
| 29 | 1 | 1 | 2 |
| 30 | 1 | 1 | 1 |
| 31 | 1 | 2 | 3 |
| 32 | 1 | 3 | 3 |
| 33 | 1 | 2 | 3 |
| 34 | 1 | 2 | 2 |
| 35 | 1 | 3 | 3 |
| 36 | 0 | 0 | 1 |
| 37 | 1 | 3 | 3 |
| 38 | 0 | 0 | 1 |

TABLE III-continued

Prophylactic action against *Erysiphe graminis* on barley upon foliar treatment.

| Compound no. | 100 ppm. | 10 ppm. | 1 ppm. |
|---|---|---|---|
| 39 | 2 | 3 | 3 |
| 40 | 1 | 3 | 3 |
| 41 | 1 | 2 | 3 |
| 42 | 1 | 1 | 1 |
| 43 | 0 | 1 | 1 |
| 44 | 0 | 0 | 1 |

C. Systemic activity against *Erysiphe cichoracearum* on gherkins.

Young gherkin plants, about 10 days old, where treated by watering of the soil with an aqueous solution of the test compound. Per plant 100 ml. were given and the total amount of test compound was 10 or 1 mg. per plant. Controls received the same amount of the solution without active ingredient. 4 Days thereafter the plants were artificially infected with *Erysiphe cichoracearum* by slightly rubbing the plants with a heavily infected leaf. Evaluation of fungal attack was done 15 days thereafter in the same manner as described in test A. The results are given in table IV wherein the compound numbers and the score system are the same as in tables I and II.

TABLE IV

Systemic activity against *Erysiphe cichoracearum* on gherkins.

| Compound no. | Scores 10 mg./plant | 1 mg./plant |
|---|---|---|
| 1 | 0 | 0 |
| 2 | 0 | 0 |
| 3 | 0 | 1 |
| 4 | 0 | 1 |
| 5 | 2 | 3 |
| 6 | 0 | 3 |
| 7 | 0 | 3 |
| 9 | 1 | 2 |
| 10 | 2 | 2 |
| 11 | 2 | 2 |
| 12 | 2 | 3 |
| 15 | 2 | 3 |
| 18 | 2 | 2 |
| 27 | 0 | 0 |
| 28 | 0 | 0 |
| 29 | 0 | 0 |

TABLE IV-continued

Systemic activity against *Erysiphe cichoracearum* on gherkins.

| Compound no. | Scores | |
|---|---|---|
| | 10 mg./plant | 1 mg./plant |
| 30 | 0 | 0 |
| 31 | 2 | 3 |
| 33 | 0 | 3 |
| 34 | 0 | 2 |
| 35 | 0 | 2 |
| 36 | 2 | 2 |

D. Prophylactic activity against *Uromyces phaseoli* on beans upon foliar treatment.

Young bean plants, about 15 cm. high, were sprayed with an aqueous solution containing 250, 100 or 10 ppm. of the test compound while controls were kept untreated. After drying, the plants were artificially infected by spraying them with a suspension of spores of *Uromyces phaseoli*. Subsequently the plants were incubated for 24 hours at 18° C. and at 95–100% relative humidity. Fungal attack was evaluated 10 days after the artificial infection in the same manner as in test A. The results are given in table V wherein the same compound numbers and the same score system as in tables I and II are used.

TABLE V

Prophylactic activity against *Uromyces phaseoli* on beans upon foliar treatment.

| Compound no. | Scores | | |
|---|---|---|---|
| | 250 ppm. | 100 ppm. | 10 ppm. |
| 1 | 1 | 2 | 3 |
| 2 | 1 | 1 | 3 |
| 3 | 1 | 1 | 2 |
| 4 | 0 | 1 | 1 |
| 5 | 0 | 0 | 3 |
| 6 | 0 | 0 | 1 |
| 7 | 0 | 0 | 2 |
| 9 | 0 | 0 | 3 |
| 10 | 0 | 2 | 3 |
| 11 | 2 | 3 | 3 |
| 28 | 1 | 2 | 3 |
| 29 | 1 | 1 | 3 |
| 30 | 1 | 2 | 3 |
| 31 | 1 | 2 | 3 |
| 32 | 1 | 2 | 3 |
| 33 | 0 | 0 | 3 |
| 34 | 1 | 2 | 2 |

Apart from their antifungal effect, the compounds of formula (I) possess valuable plant growth regulating properties. Depending on different factors such as the species of the plants under investigation and the dose of active ingredient administered, the observed effect may be growth stimulation or growth inhibition. As such the compounds of this invention are useful as plant growth regulators and this useful property is naturally intended to be also within the scope of this invention.

In view of the aforementioned antifungal and growth-regulating activities this invention provides valuable compositions comprising the subject triazoles (I) or the acid addition salts thereof as the active ingredient in a solvent or a solid, semi-solid or liquid diluent or carrier, and, in addition, it provides an effective method of combatting fungal growth by use of an effective antifungal amount of such triazoles (I) or salts thereof. The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate in the form of prepared chalk or ground limestone, kaolin, bole, bentonite, talcum, kieselguhr and boric acid; powdered cork, sawdust, and other fine pulverous materials of vegetable origin are also suitable carrier substances.

The active ingredient is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, polyethylene glycol, isopropanol, dimethylsulfoxide, hydrogenated naphthalenes and alkylated naphthalenes. It is, of course, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi, e.g., in closed chambers and storage rooms, and for application to vegetation of eradicating or for preventing infections by fungi.

The subject compounds and compositions thereof can be applied by conventional methods. For example, a fungal growth or a material to be treated or to be protected against attack by fungus can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, powder, ointment, emulsion, and the like forms, a high activity over a very high range of dilution is observed. For example, concentrations of the active ingredient ranging from 0.1–10 percent by weight, based on the weight of composition employed, have been found effective in combatting fungi. Of course, higher concentrations may also be employed as warranted by the particular situation.

The following examples are intended to illustrate, but not to limit, the scope of the present invention. Unless otherwise stated, all parts are by weight.

EXAMPLE I

To a stirred and refluxing mixture of 122 parts of 4-chloro-3-methylphenol, 214.1 parts of 1,3-dibromopropane and 850 parts of water added dropwise, during a one hour-period, a solution of 34 parts of sodium hydroxide in 213 parts of water. Upon completion, stirring at reflux is continued overnight. The reaction mixture is cooled to room temperature and the product is extracted with 765 parts of benzene. The extract is washed with a sodium hydroxide solution 10%, dried, filtered and evaporated. The residue is distilled twice, yielding 114 parts of 4-(3-bromopropoxy)-1-chloro-2-methylbenzene; bp. 119° C. at 0.6 mm. pressure.

EXAMPLE II

Following the procedure of Example I and using an equivalent amount of an appropriate substituted phenol in place of the 4-chloro-3-methylphenol used therein the following intermediate compounds are prepared:

1-(3-bromopropoxy)-4-chloro-2-methylbenzene;bp. 115°–116° C. at 0.6 mm. pressure;

2-(3-bromopropoxy)-1,5-dichloro-3-methylbenzene;bp. 118° C. at 0.6 mm. pressure;

4-(3-bromopropoxy)-3-chloro-[1,1'-biphenyl];

2-bromo-1-(3-bromopropoxy)-4-methylbenzene;bp. 123°–126° C. at 0.8 mm. pressure; and 1,3,5-tribromo-2-(3-bromopropoxy)benzene.bp. 160°–177° C.

EXAMPLE III

To a stirred and cooled (water-bath) suspension of 7 parts of a sodium hydride dispersion 78% and 75 parts of dimethylsulfoxide is added dropwise, during a 30 minutes-period, a solution of 37 parts of 2,4-dichlorobenzeneacetonitrile in 100 parts of dimethylsulfoxide. The whole is stirred for 30 minutes while cooling in a water-bath. Then there is added dropwise, during a 30 minutes-period, a solution of 56 parts of 1-bromo-4-(2-bromoethoxy)benzene in 125 parts of dimethylsulfoxide and stirring is continued for another 30 minutes. The reaction mixture is poured onto water and the product is extracted twice with 2,2'-oxybispropane. The combined extracts are washed twice with water, dried, filtered and evaporated. The residue is triturated in petroleumether. The product is filtered off and crystallized from ethanol, yielding 38 parts of α-[2-(4-bromophenoxy)ethyl]-2,4-dichlorobenzeneacetonitrile; mp. 73.9° C.

EXAMPLE IV

A mixture of 18.5 parts of 2,4-dichlorobenzeneacetonitrile and 180 parts of N,N-dimethylformamide is stirred and cooled in an ice-bath while nitrogen gas is introduced. 3.2 Parts of a sodium hydroxide solution 78% are added portionwise and the whole is stirred for one hour. Then there are added dropwise, during a one hour-period, 17.8 parts of (bromomethyl)cyclohexane while still cooling and while nitrogen gas is still introduced. Upon completion, stirring is continued for 2 hours at room temperature. The reaction mixture is poured onto water. The precipitated product is filtered off and triturated in a mixture of methanol and water. The product is filtered off and dried, yielding 25.5 parts of 2,4-dichloro-α-(cyclohexylmethyl)benzeneacetonitrile; mp. 58.8° C.

EXAMPLE V

By repeating the procedure of Example IV and using equivalent amounts of the appropriate starting materials, there are prepared:

α-(3-butenyl)-2,4-dichlorobenzeneacetonitrile; bp. 104°–108° C. at 0.1 mm. pressure; and 2,4-dichloro-α-(2-cyclopentylethyl)benzeneacetonitrile; bp. 130°–135° C. at 0.05 mm. pressure.

EXAMPLE VI

To a stirred and cooled (ice-bath) mixture of 27.5 parts of 2,4-dibromobenzeneacetonitrile, 135 parts of N,N-dimethylformamide and 67.5 parts of benzene are added portionwise 3.2 parts of sodium hydride dispersion 78% while nitrogen gas is introduced. After stirring for one hour, 14 parts of 1-bromobutane are added dropwise. Upon completion, stirring is continued for 2 hours at room temperature. The reaction mixture is poured onto water and the product is extracted twice with 2,2'-oxybispropane. The combined extracts are washed twice with water, dried, filtered and evaporated. The residue is distilled, yielding 22 parts of 2,4-dibromo-α-butylbenzeneacetonitrile; bp. 124° C. at 0.05 mm. pressure.

EXAMPLE VII

By repeating the procedure of Example VI and using an equivalent amount of respectively an appropriate bromide and an appropriate arylacetonitrile in place of the 1-bromobutane and the 2,4-dibromobenzeneacetonitrile used therein the following compounds are prepared:

2,4-dichloro-α-[3-(4-chloro-3-methylphenoxy)propyl]benzeneacetonitrile; bp. 216°–219° C. at 0.05 mm. pressure;

2,4-dichloro-α-[3-(3,5-dichlorophenoxy)propyl]benzeneacetonitrile; bp. 210°–215° C. at 0.05 mm. pressure;

2,4-dichloro-α-[3-(2-naphthalenyloxy)propyl]benzeneacetonitrile; mp. 100° C.;

α-[3-(2-bromophenoxy)propyl]-2,4-dichlorobenzeneacetonitrile; mp. 61.2° C.;

2,4-dichloro-α-[3-(4-chloro-2-methylphenoxy)propyl]benzeneacetonitrile; mp. 73° C.;

2,4-dichloro-α-[3-(2,4-dichloro-6-methylphenoxy)propyl]benzeneacetonitrile; bp. 212°–216° C. at 0.05 mm. pressure;

2,4-dichloro-α-[3-(3-chloro-[1,1'-biphenyl]-4-yloxy)propyl]benzeneacetonitrile; mp. 70.3° C.;

α-[3-(2-bromo-4-methylphenoxy)propyl]-2,4-dichlorobenzeneacetonitrile; bp. 215°–219° C. at 0.05 mm. pressure; and 2,4-dichloro-α-[3-(2,4,6-tribromophenoxy)propyl]benzeneacetonitrile; mp. 85.2° C.

EXAMPLE VIII

To a stirred mixture of 18.5 parts of 2,4-dichlorobenzeneacetonitrile, 90 parts of N,N-dimethylformamide and 67.5 parts of benzene are added portionwise 3.2 parts of a sodium hydride dispersion 78% while nitrogen gas is introduced. After stirring for 1 hour at room temperature, 14.5 parts of (2-chloroethyl)cyclohexane are added. The whole is stirred first for 5 hours at 40°–50° C. and further overnight at room temperature. The reaction mixture is poured onto water and the product is extracted twice with 2,2'-oxybispropane. The combined extracts are washed twice with water, dried, filtered and evaporated. The residue is distilled, yielding 16 parts (54%) of 2,2'-dichloro-α-(2-cyclohexylethyl)benzeneacetonitrile; bp. 145°–148° C. at 0.05 mm. pressure.

EXAMPLE IX

Following the procedure of Example VIII and using equivalent amounts of the appropriate starting materials, there are prepared:
α-(2,4-dichlorophenyl)-[1,1'-biphenyl]-4-propanenitrile; bp. 215°–230° C. at 0.05 mm. pressure;
2,4-dichloro-α-(2,4-dichlorophenyl)benzenebutanenitrile as an oily residue;
4-chloro-α-(4-chlorophenyl)benzenebutanenitrile as an oily residue;
4-chloro-α-(4-methylphenyl)benzenebutanenitrile; bp. 175°–178° C. at 0.1 mm. pressure;
α-(4-bromophenyl)-2-methoxybenzenebutanenitrile as an oily residue;
α-(4-bromophenyl)-4-chlorobenzenebutanenitrile as an oily residue;
4-chloro-α-(4-fluorophenyl)benzenebutanenitrile; bp. 165°–168° C. at 0.1 mm. pressure;
α-(4-fluorophenyl)-4-methylbenzenebutanenitrile; bp. 160°–165° C. at 0.3 mm. pressure;
4-bromo-α-(2-chlorophenyl)benzenebutanenitrile; bp. 176°–180° C. at 0.1 mm. pressure; and
4-bromo-α-(4-bromophenyl)benzenebutanenitrile as an oily residue.

EXAMPLE X

120 Parts of methanol are saturated with gaseous hydrogen chloride while cooling in an ice-bath. Then there are added 22 parts of 2,4-dibromo-α-butylbenzeneacetonitrile and the whole is stirred and refluxed overnight. The reaction mixture is cooled and poured onto water. The product is extracted with 2,2'-oxybispropane. The extract is washed with water, dried, filtered and evaporated. The residue is distilled, yielding 16.5 parts (68%) of methyl 2,4-dibromo-α-butylbenzeneacetate; bp. 125° C. at 0.1 mm. pressure.

EXAMPLE XI

Following the procedure of Example X, the following esters are prepared starting from the appropriate nitriles:
methyl α-(3-butenyl)-2,4-dichlorobenzeneacetate as a residue;
methyl 2,4-dichloro-α-(cyclohexylmethyl)benzeneacetate as a residue;
methyl 2,4-dichloro-α-(2-cyclopentylethyl)benzeneacetate as a residue;
methyl 2,4-dichloro-α-(2-cyclohexylethyl)benzeneacetate as a residue;
methyl α-(2,4-dichlorophenyl)-[1,1'-biphenyl]-4-propanoate as an oily residue;
methyl 2,4-dichloro-α-(2,4-dichlorophenyl)benzenebutanoate as an oily residue;
methyl 4-chloro-α-(4-chlorophenyl)benzenebutanoate; bp. 175°–178° C. at 0.1 mm. pressure;
methyl 2,4-dichloro-α-[3-(2-naphthalenyloxy)propyl]benzeneacetate; mp. 69.7° C.;
methyl 4-chloro-α-(4-methylphenyl)benzenebutanoate as an oily residue;
methyl α-(4-bromophenyl)-2-methoxybenzenebutanoate; bp. 178°–185° C. at 0.1 mm. pressure;
methyl α-(4-bromophenyl)-4-chlorobenzenebutanoate; bp. 177°–180° C. at 0.1 mm. pressure;
methyl 4-chloro-α-(4-fluorophenyl)benzenebutanoate as an oily residue;
methyl α-(4-fluorophenyl)-4-methylbenzenebutanoate as a residue;
methyl 4-bromo-α-(2-chlorophenyl)benzenebutanoate as an oily residue;
methyl 4-bromo-α-(4-bromophenyl)benzenebutanoate as an oily residue;
methyl α-[2-(4-bromophenoxy)ethyl]-2,4-dichlorobenzeneacetate as a residue;
methyl 2,4-dichloro-α-[3-(3,5-dichlorophenoxy)propyl]benzeneacetate as a residue;
methyl 2,4-dichloro-α-[3-(4-chloro-3-methylphenoxy)propyl]benzeneacetate as a residue;
methyl α-[3-(2-bromophenoxy)propyl]-2,4-dichlorobenzeneacetate as a residue;
methyl 2,4-dichloro-α-[3-(4-chloro-2-methylphenoxy)propyl]benzeneacetate as an oily residue;
methyl 2,4-dichloro-α-[3-(2,4-dichloro-6-methylphenoxy)propyl]benzeneacetate as a residue;
methyl α-[3-(2-bromo-4-methylphenoxy)propyl]-2,4-dichlorobenzeneacetate as a residue;
methyl 2,4-dichloro-α-[3-(3-chloro-[1,1'-biphenyl]-4-yloxy)propyl]benzeneacetate; and
methyl 2,4-dichloro-α-[3-(2,4,6-tribromophenoxy)propyl]benzeneacetate as an oily residue.

EXAMPLE XII

To a stirred mixture of 22 parts of methyl 2,4-dichlorobenzeneacetate and 135 parts of N,N-dimethylformamide are added 3.1 parts of sodium hydride dispersion 78% while nitrogen gas is introduced. The whole is stirred till foaming has ceased and cooled in an ice-bath. Then there are added dropwise 16 parts of iodomethane. Upon completion, stirring is continued for 3 hours at room temperature. The reaction mixture is poured onto water and the product is extracted with 2,2'-oxybispropane. The extract is washed with water, dried, filtered and evaporated, yielding 20 parts (80%) of methyl 2,4-dichloro-α-methylbenzeneacetate as a residue.

EXAMPLE XIII

To a stirred mixture of 22 parts of methyl 2,4-dichlorobenzeneacetate and 135 parts of N,N-dimethylformamide are added 3.1 parts of a sodium hydride dispersion 78% while nitrogen gas is introduced. After stirring till foaming has ceased, there are added 15 parts of 2-bromopropane and the whole is stirred for 3 hours at room temperature. The reaction mixture is poured onto water and the product is extracted twice with 2,2'-oxybispropane. The combined extracts are washed with water, dried, filtered and evaporated, yielding 24.5 parts (94%) of methyl 2,4-dichloro-α-(1-methylethyl)-benzeneacetate as a residue.

To 140 parts of 1,1'-oxybisethane are added 3 parts of lithium aluminium hydride. Then there is added dropwise a solution of 24.5 parts of methyl 2,4-dichloro-α-(1-methylethyl)benzeneacetate in 35 parts of 1,1'-oxybisethane while cooling in a water-bath. Upon completion, stirring is continued overnight at room temperature. There are added dropwise successively 3 parts of a sodium hydroxide solution 50% and 1 part of water, and the whole is stirred for one hour at room temperature. The mixture is filtered over hyflo and the filter-cake is washed with 2,2'-oxybispropane. The filtrate is evaporated, yielding 20.5 parts (93.5%) of 2,4-dichloro-β-(1-methylethyl)benzeneethanol as a residue.

EXAMPLE XIV

A mixture of 16.5 parts of methyl 2,4-dibromo-α-butylbenzeneacetate, 11.5 parts of lithium iodide dihydrate and 180 parts of acetonitrile is stirred till all solid enters solution. Then there are added portionwise 3.6 parts of sodium borohydride. Upon completion, the whole is heated to reflux and stirring is continued overnight at reflux temperature. After cooling, the reaction mixture is acidified with a diluted hydrochloric acid solution and poured onto water. The product is extracted with 2,2'-oxybispropane. The extract is washed with water, dried, filtered and evaporated, yielding 15 parts (100%) of 2,4-dibromo-β-butylbenzeneethanol as a residue.

EXAMPLE XV

Following the procedure of Example XIV and using an equivalent amount of an appropriate methyl ester as a starting material the following alcohols are obtained as a residue:

β-(3-butenyl)-2,4-dichlorobenzeneethanol;
2,4-dichloro-β-methylbenzeneethanol;
2,4-dichloro-β-(cyclohexylmethyl)benzeneethanol;
2,4-dichloro-β-(2-cyclopentylethyl)benzeneethanol;
2,4-dichloro-β-(2-cyclohexylethyl)benzeneethanol;
β-(2,4-dichlorophenyl)-[1,1'-biphenyl]-4-propanol;
2,4-dichloro-β-(2,4-dichlorophenyl)benzenebutanol;
4-chloro-β-(4-chlorophenyl)benzenebutanol;
4-chloro-β-(4-methylphenyl)benzenebutanol;
β-(4-bromophenyl)-2-methoxybenzenebutanol;
β-(4-bromophenyl)-4-chlorobenzenebutanol;
4-chloro-β-(4-fluorophenyl)benzenebutanol;
β-(4-fluorophenyl)-4-methylbenzenebutanol;
4-bromo-β-(2-chlorophenyl)benzenebutanol;
4-bromo-β-(4-bromophenyl)benzenebutanol;
β-[2-(4-bromophenoxy)ethyl]-2,4-dichlorobenzeneethanol;
2,4-dichloro-β-[3-(3,5-dichlorophenoxy)propyl]benzeneethanol;
β-[3-(2-bromophenoxy)propyl]-2,4-dichlorobenzeneethanol;
2,4-dichloro-β-[3-(4-chloro-3-methylphenoxy)propyl]-benzeneethanol;
2,4-dichloro-β-[3-(4-chloro-2-methylphenoxy)propyl]-benzeneethanol;
2,4-dichloro-β-[3-(2-naphthalenyloxy)propyl]benzeneethanol;
β-[3-(2-bromo-4-methylphenoxy)propyl]-2,4-dichlorobenzeneethanol;
2,4-dichloro-β-[3-(2,4-dichloro-6-methylphenoxy)propyl]benzeneethanol;
2,4-dichloro-β-[3-(3-chloro-[1,1'-biphenyl]-4-yloxy)propyl]benzeneethanol; and
2,4-dichloro-β-[3-(2,4,6-tribromophenoxy)propyl]benzeneethanol.

EXAMPLE XVI

To a stirred and cooled (ice-bath) mixture of 22 parts of 2,4-dichloro-β-(cyclohexylmethyl)benzeneethanol and 50 parts of pyridine are added dropwise 8.8 parts of methanesulfonyl chloride. Upon completion, stirring is continued for 3 hours at room temperature. The reaction mixture is poured onto water and the product is extracted twice with trichloromethane. The combined extracts are washed twice with a diluted hydrochloric acid solution and once with water, dried, filtered and evaporated. The residue is crystallized from 2,2'-oxybispropane, yielding 16.5 parts of 3-cyclohexyl-2-(2,4-dichlorophenyl)propyl methanesulfonate; mp. 105.1° C.

EXAMPLE XVII

Following the procedure of Example XVI the following methanesulfonates are prepared starting from the corresponding alcohols:

2-(2,4-dichlorophenyl)-5-hexenyl methanesulfonate as a residue;
2-(2,4-dichlorophenyl)propyl methanesulfonate as a residue;
2-(2,4-dichlorophenyl)-3-methylbutyl methanesulfonate as a residue;
2-(2,4-dibromophenyl)hexyl methanesulfonate as a residue;
4-cyclopentyl-2-(2,4-dichlorophenyl)butyl methanesulfonate; mp. 65.4° C.;
4-cyclohexyl-2-(2,4-dichlorophenyl)butyl methanesulfonate; mp. 44.4° C.;
3-([1,1'-biphenyl]-4-yl)-2-(2,4-dichlorophenyl)propyl methanesulfonate as an oily residue;
2,4-bis(2,4-dichlorophenyl)butyl methanesulfonate as an oily residue;
2,4-bis(4-chlorophenyl)butyl methanesulfonate as a residue;
4-(4-chlorophenyl)-2-(4-methylphenyl)butyl methanesulfonate as an oily residue;
2-(4-bromophenyl)-4-(2-methoxyphenyl)butyl methanesulfonate as an oily residue;
2-(4-bromophenyl)-4-(4-chlorophenyl)butyl methanesulfonate as an oily residue;
4-(4-chlorophenyl)-2-(4-fluorophenyl)butyl methanesulfonate as an oily residue;
2-(4-fluorophenyl)-4-(4-methylphenyl)butyl methanesulfonate as an oily residue; and
4-(4-bromophenyl)-2-(2-chlorophenyl)butyl methanesulfonate as an oily residue.

EXAMPLE XVIII

A mixture of 30.4 parts of β-[2-(4-bromophenoxy)ethyl]-2,4-dichlorobenzeneethanol, 11.5 parts of methanesulfonyl chloride, 100 parts of pyridine and 70 parts of 2,2'-oxybispropane is stirred overnight at room temperature. The reaction mixture is poured onto water and the product is extracted twice with 2,2'-oxybispropane. The combined extracts are washed successively with a diluted hydrochloric acid solution and twice with water, dried, filtered and evaporated, yielding 34 parts of 4-(4-bromophenoxy)-2-(2,4-dichlorophenyl)butyl methanesulfonate as a residue.

EXAMPLE XIX

Following the procedure of Example XVIII the following methanesulfonates are prepared starting from the corresponding alcohols:

5-(3,5-dichlorophenoxy)-2-(2,4-dichlorophenyl)pentyl methanesulfonate as a residue;

5-(2-bromophenoxy)-2-(2,4-dichlorophenyl)pentyl methanesulfonate as a residue;

5-(4-chloro-3-methylphenoxy)-2-(2,4-dichlorophenyl)pentyl methanesulfonate as a residue;

2-(2,4-dichlorophenyl)-5-(2-naphthalenyloxy)pentyl methanesulfonate as a residue;

5-(4-chloro-2-methylphenoxy)-2-(2,4-dichlorophenyl)pentyl methanesulfonate as a residue;

5-(2-bromo-4-methylphenoxy)-2-(2,4-dichlorophenyl)pentyl methanesulfonate as an oily residue;

5-(2,4-dichloro-6-methylphenoxy)-2-(2,4-dichlorophenyl)pentyl methanesulfonate as a residue;

5-(2-chloro-[1,1'-biphenyl]-4-yloxy)-2-(2,4-dichlorophenyl)pentyl methanesulfonate as a residue;

2,4-bis(4-bromophenyl)butyl methanesulfonate as an oily residue; and 2-(2,4-dichlorophenyl)-5-(2,4,6-tribromophenoxy)pentyl methanesulfonate as a residue.

EXAMPLE XX

To a stirred suspension of 3.4 parts of a sodium hydride dispersion 78% in 90 parts of N,N-dimethylformamide are added portionwise, during a 5 minutes-period, 6.9 parts of 1H-1,2,4-triazole. After stirring for 10 minutes at room temperature, there are added 19.1 parts of 4-chloro-α-(chloromethyl)benzenemethanol. The whole is stirred and refluxed for 8 hours. The reaction mixture is cooled and poured onto water. The product is extracted with dichloromethane. The extract is washed with water, dried, filtered and evaporated. The residue is triturated in 2,2'-oxybispropane. The product is filtered off and crystallized from methylbenzene, yielding 17.3 parts (77%) of α-(4-chlorophenyl)-1H-1,2,4-triazole-1-ethanol; mp. 119° C.

EXAMPLE XXI

To a stirred mixture of 14 parts of 1H-1,2,4-triazole and 225 parts of N,N-dimethylformamide are added 6.2 parts of a sodium hydride dispersion 78%. When foaming has ceased, there are added 19.5 parts of 2-(2,4-dichlorophenyl)propyl methanesulfonate and stirring is continued for 6 hours at reflux. The reaction mixture is cooled, poured onto water and the product is extracted twice with 2,2'-oxybispropane. The combined extracts are washed with water, dried, filtered and evaporated. The residue is crystallized from petroleumether. The product is filtered off and dried, yielding 10.2 parts (58%) of 1-[2-(2,4-dichlorophenyl)propyl]-1H-1,2,4-triazole; mp. 79.5° C.

EXAMPLE XXII

To a stirred mixture of 16 parts of 1H-1,2,4-triazole in 225 parts of N,N-dimethylformamide are added 6.8 parts of a sodium hydride dispersion 78% and the whole is stirred till foaming has ceased. Then there are added 23.5 parts of 2-(2,4-dichlorophenyl)-3-methylbutyl methanesulfonate and stirring is continued for 24 hours at reflux temperature. The reaction mixture is cooled and poured onto water. The product is extracted twice with 2,2'-oxybispropane. The combined extracts are washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the nitrate salt in 2,2'-oxybispropane. The salt is filtered off and crystallized from a mixture of 4-methyl-2-pentanone and 2,2'-oxybispropane, yielding 18.4 parts (70%) of 1-[2-(2,4-dichlorophenyl)-3-methylbutyl]-1H-1,2,4-triazole nitrate; mp. 147.1° C.

EXAMPLE XXIII

Following the procedure of Example XXII and using an equivalent amount of an appropriate methanesulfonate in place of the 2-(2,4-dichlorophenyl)-3-methylbutyl methanesulfonate used therein, the following triazoles and triazole nitrate salts are prepared:

1-[2-(2,4-dichlorophenyl)butyl]-1H-1,2,4-triazole; mp. 70.2° C.;

1-[2-(2,4-dichlorophenyl)pentyl]-1H-1,2,4-triazole; mp. 62.7° C.;

1-[2-(2,4-dibromophenyl)hexyl]-1H-1,2,4-triazole nitrate; mp. 141.7° C.;

1-[2-(2,4-dichlorophenyl)-3-methylpentyl]-1H-1,2,4-triazole nitrate; mp. 116.6° C.;

1-[2-(2,4-dichlorophenyl)-4-methylpentyl]-1H-1,2,4-triazole nitrate; mp. 146.8° C.;

1-[2-(2,4-dichlorophenyl)heptyl]-1H-1,2,4-triazole nitrate; mp. 144.6° C.;

1-[2-(2,4-dichlorophenyl)decyl]-1H-1,2,4-triazole nitrate; mp. 116.6° C.;

1-[2-cyclopentyl-2-(2,4-dichlorophenyl)ethyl]-1H-1,2,4-triazole nitrate; mp. 149.2° C.;

1-[2-cyclohexyl-2-(2,4-dichlorophenyl)ethyl]-1H-1,2,4-triazole; mp. 79.2° C.;

1-[3-cyclohexyl-2-(2,4-dichlorophenyl)propyl]-1H-1,2,4-triazole nitrate hemihydrate; mp. 124.3° C.;

1-[4-cyclohexyl-2-(2,4-dichlorophenyl)butyl]-1H-1,2,4-triazole; mp. 96.5° C.;

1-[2-(2,4-dichlorophenyl)-4-pentenyl]-1H-1,2,4-triazole nitrate; mp. 139.7° C.; and 1-[2-(2,4-dichlorophenyl)-5-hexenyl]-1H-1,2,4-triazole mononitrate; mp. 114.8° C.

EXAMPLE XXIV

To a stirred mixture of 3.8 parts of a sodium hydride dispersion 78% and 90 parts of N,N-dimethylformamide is added dropwise a solution of 21 parts of 2,4-bis(4-chlorophenyl)butyl methanesulfonate in 45 parts of N,N-dimethylformamide. After stirring for 15 minutes at room temperature, there is added a solution of 7.6 parts of 1H-1,2,4-triazole in 45 parts of N,N-dimethylformamide. The whole is heated slowly to 100° C. and stirring is continued for 2 hours at 100° C. The reaction mixture is poured onto water and the product is extracted with 1,1'-oxybisethane. The extract is washed with water, dried, filtered and evaporated. The oily residue is purified by column-chromatography over silica gel using a mixture of trichloromethane and methanol (97.5:2.5 by volume) as eluent. The pure fractions are collected and the eluent is evaporated. The oily residue is converted into the hydrochoride salt in 2,2'-oxybispropane. The salt is filtered off and crystallized from a mixture of methanol and 2,2'-oxybispropane, yielding 7 parts (32.5%) of 1-[2,4-bis(4-chlorophenyl)butyl]-1H-1,2,4-triazole hydrochloride; mp. 173.4° C.

EXAMPLE XXV

Following the procedure of Example XXIV and using an equivalent amount of an appropriate methanesulfonate in place of the 2,4-bis(4-chlorophenyl)butyl methanesulfonate, the following triazoles and triazole hydrochloride salts are prepared:

1-[3-([1,1'-biphenyl]-4-yl)-2-(2,4-dichlorophenyl)propyl]-1,2,4-triazole hydrochloride; mp. 175.5° C.;
1-[4-(4-chlorophenyl)-2-(4-methylphenyl)butyl]-1H-1,2,4-triazole hydrochloride; mp. 170° C.;
1-[2-(4-bromophenyl)-4-(2-methoxyphenyl)butyl]-1H-1,2,4-triazole hydrochloride; mp. 153.2° C.;
1-[2-(4-bromophenyl)-4-(4-chlorophenyl)butyl]-1H-1,2,4-triazole; mp. 87.6° C.;
1-[4-(4-chlorophenyl)-2-(4-fluorophenyl)butyl]-1H-1,2,4-triazole hydrochloride; mp. 171.8° C.;
1-[2-(4-fluorophenyl)-4-(4-methylphenyl)butyl]-1H-1,2,4-triazole hydrochloride; mp. 128.6° C.;
1-[4-(4-bromophenyl)-2-(2-chlorophenyl)butyl]-1H-1,2,4-triazole hydrochloride; mp. 142.6° C.; and
1-[2,4-bis(4-bromophenyl)butyl]-1H-1,2,4-triazole hydrochloride; mp. 163° C.

EXAMPLE XXVI

A mixture of 6.9 parts of 1H-1,2,4-triazole, 3.4 parts of a sodium hydride dispersion 78% and 90 parts of N,N-dimethylformamide is stirred for 10 minutes at room temperature. Then there is added a solution of 19.9 parts of 5-(2-bromo-4-methylphenoxy)-2-(2,4-dichlorophenyl)pentyl methanesulfonate in 45 parts of N,N-dimethylformamide. Stirring is continued for 2 hours at 100° C. The reaction mixture is allowed to cool to room temperature and poured onto water. The product is extracted twice with 1,1'-oxybisethane. The combined extracts are washed with water and acidified with a concentrated nitric acid solution. The formed nitrate salt is filtered off and crystallized from a mixture of acetonitrile and 2,2'-oxybispropane, yielding 13.3 parts (64%) of 1-[5-(2-bromo-4-methylphenoxy)-2-(2,4-dichlorophenyl)pentyl]-1H-1,2,4-triazole nitrate; mp. 119.6° C.

EXAMPLE XXVII

Following the procedure of Example XXVI the following triazole nitrate salts are prepared starting from 1H-1,2,4-triazole and an appropriate methanesulfonate:

1-[5-(3,5-dichlorophenoxy)-2-(2,4-dichlorophenyl)pentyl]-1H-1,2,4-triazole nitrate; mp. 145.3° C.;
1-[4-(4-bromophenoxy)-2-(2,4-dichlorophenyl)butyl]-1H-1,2,4-triazole nitrate; mp. 144.6° C.;
1-[5-(2-bromophenoxy)-2-(2,4-dichlorophenyl)pentyl]-1H-1,2,4-triazole nitrate; mp. 123.2° C.;
1-[2-(2,4-dichlorophenyl)-5-(2-naphthalenyloxy)pentyl]-1H-1,2,4-triazole nitrate; mp. 136.8° C.;
1-[5-(4-chloro-3-methylphenoxy)-2-(2,4-dichlorophenyl)pentyl]-1H-1,2,4-triazole nitrate; mp. 140° C.;
1-[5-(4-chloro-2-methylphenoxy)-2-(2,4-dichlorophenyl)pentyl]-1H-1,2,4-triazole nitrate; mp. 123.1° C.;
1-[5-(2,4-dichloro-6-methylphenoxy)-2-(2,4-dichlorophenyl)pentyl]-1H-1,2,4-triazole nitrate; mp. 153.4° C.;
1-[5-(3-chloro-[1,1'-biphenyl]-4-yloxy)-2-(2,4-dichlorophenyl)pentyl]-1H-1,2,4-triazole nitrate; mp. 135.3° C.; and
1-[2-(2,4-dichlorophenyl)-5-(2,4,6-tribromophenoxy)pentyl]-1H-1,2,4-triazole nitrate; mp. 166.5° C.:

EXAMPLE XXVIII

To a stirred sodium methoxide solution, previously prepared starting from 3.9 parts of sodium in 40 parts of methanol, is added a mixture of 12 parts of 1H-1,2,4-triazole and 225 parts of N,N-dimethylformamide. The methanol is distilled off till an internal temperature of 150° C. is reached. After cooling to 100° C., there are added 18.5 parts of 2-(2,4-dichlorophenyl)hexyl methanesulfonate and stirring at 100° C. is continued for 2 hours. The reaction mixture is cooled, poured onto water and the product is extracted three times with 2,2'-oxybispropane. The combined extracts are washed with water, dried, filtered and evaporated. The residue is purified by column-chromatography over silica gel using trichloromethane as eluent. The pure fractions are collected and the eluent is evaporated. The residue is converted into the nitrate salt in 2,2'-oxybispropane and petroleumether. The salt is filtered off and crystallized from a mixture of 2-propanone, 2,2'-oxybispropane and petroleumether, yielding 11.6 parts (56%) of 1-[2-(2,4-dichlorophenyl)hexyl]-1H-1,2,4-triazole nitrate; mp. 128.3° C.

EXAMPLE XXIX

Following the procedure of Example XXVIII there are prepared:

1-[4-cyclopentyl-2-(2,4-dichlorophenyl)butyl]-1H-1,2,4-triazole; mp. 71° C., by the reaction of 1H-1,2,4-triazole with 4-cyclopentyl-2-(2,4-dichlorophenyl)butyl methanesulfonate; and
1-[2,4-bis(2,4-dichlorophenyl)butyl]-1H-1,2,4-triazole hydrochloride; mp. 158.7° C., by the reaction of 1H-1,2,4-triazole with 2,4-bis(2,4-dichlorophenyl)butyl methanesulfonate.

EXAMPLE XXX

To a stirred sodium methoxide solution, prepared starting from 1.6 parts of sodium in 56 parts of methanol, are added 4.8 parts of 1H-1,2,4-triazole. 40 Parts of methanol are distilled off at normal pressure. After the addition of 80 parts of 4-methyl-2-pentanone, another 28 parts of solvent are distilled off. Then there are added 22 parts of 3-(4-chlorophenyl)-2-(2,4-dichlorophenyl)propyl methanesulfonate and 90 parts of N,N-dimethylformamide and the whole is stirred and refluxed overnight. The reaction mixture is allowed to cool to room temperature and poured onto water. The product is extracted twice with 2,2'-oxybispropane. The combined extracts are washed twice with water and an excess of a concentrated nitric acid solution is added. The formed nitrate salt is filtered off and crystallized from 4-methyl-2-pentanone, yielding 6.6 parts (27%) of 1-[3-(4-chlorophenyl)-2-(2,4-dichlorophenyl)propyl]-1H-1,2,4-triazole nitrate; mp. 174.8° C.

EXAMPLE XXXI

Following the procedure of Example XXX there is prepared 1-[3-(2-bromophenyl)-2-(2,4-dichlorophenyl)propyl]-1H-1,2,4-triazole nitrate; mp. 168.4° C., by the reaction of 1H-1,2,4-triazole with 3-(2-bromophenyl)-2-(2,4-dichlorophenyl)propyl methanesulfonate.

EXAMPLE XXXII

A mixture of 5.2 parts of α-(2,4-dichlorophenyl)-1H-1,2,4-triazole-1-ethanol, 45 parts of N,N-dimethylformamide and 45 parts of benzene is stirred till all solid enters solution. After cooling in an ice-bath, there is added portionwise 1 part of a sodium hydride dispersion 78% and the whole is stirred till gas-evolution has ceased. Then there are added 2.75 parts of 1-bromopropane and stirring is continued first for 2 hours while cooling in an ice-bath and further overnight at room temperature. The reaction mixture is poured onto ice-water and the product is extracted with 1,1'-oxybisethane. The extract is washed with water, dried, filtered and evaporated. The oily residue is purified by column-chromatography over silica gel using a mixture of trichloromethane and methanol (95:5 by volume) as eluent. The pure fractions are collected and the eluent is evaporated. The oily residue is converted into the nitrate salt in 2,2'-oxybispropane. The salt is filtered off and crystallized from a mixture of 2-propanol and 2,2'-oxybispropane, yielding 2.5 parts (34.4%) of 1-[2-(2,4-dichlorophenyl)-2-propoxyethyl]-1H-1,2,4-triazole nitrate; mp. 140° C.

EXAMPLE XXXIII

Following the procedure of Example XXXII and using equivalent amounts of the appropriate starting materials, the following compounds are prepared:
1-[2-(2,4-dichlorophenyl)-2-ethoxyethyl]-1H-1,2,4-triazole nitrate; mp. 136.7° C.;
1-[2-butoxy-2-(2,4-dichlorophenyl)ethyl]-1H-1,2,4-triazole nitrate; mp. 148.1° C.;
1-[2-(2,4-dichlorophenyl)-2-(hexyloxy)ethyl]-1H-1,2,4-triazole nitrate; mp. 140.1° C.;
1-[2-(2,4-dichlorophenyl)-2-(heptyloxy)ethyl]-1H-1,2,4-triazole nitrate; mp. 139.2° C.; and
1-[2-(2,4-dichlorophenyl)-2-(2-propenyloxy)ethyl]-1H-1,2,4-triazole nitrate; mp. 132.5° C.

EXAMPLE XXXIV

A mixture of 4.5 parts of α-(4-chlorophenyl)-1H-1,2,4-triazole-1-ethanol, 50 parts of dimethyl sulfoxide and 45 parts of benzene is stirred till all solid enters solution. Then there is added 1 part of a sodium hydride dispersion 78% and stirring is continued till foaming has ceased. After stirring and heating for one hour at 40°-50° C., the mixture is cooled to room temperature and 5.4 parts of bromoethane are added. The whole is stirred overnight at room temperature, poured onto ice-water and the product is extracted with 1,1'-oxybisethane. The extract is washed with water, dried, filtered and evaporated. The oily residue is purified by column-chromatography over silica gel using a mixture of trichloromethane and methanol (95:5 by volume) as eluent. The pure fractions are collected and the eluent is evaporated. The oily residue is converted into the nitrate salt in 2,2'-oxybispropane and hexane (1:5 by volume). The salt is filtered off and crystallized from a mixture of 2-propanol and hexane, yielding 3 parts (47.6%) of 1-[2-(4-chlorophenyl)-2-ethoxyethyl]-1H-1,2,4-triazole mononitrate; mp. 118.7° C.

EXAMPLE XXXV

Following the procedure of Example XXXIV and using equivalent amounts of the appropriate starting materials the following compounds are prepared:
1-[2-butoxy-2-(4-chlorophenyl)ethyl]-1H-1,2,4-triazole mononitrate; mp. 107.1° C.;
1-[2-(2,4-dichlorophenyl)-2-(pentyloxy)ethyl]-1H-1,2,4-triazole nitrate; mp. 149° C.;
1-[2-(4-chlorophenyl)-2-(pentyloxy)ethyl]-1H-1,2,4-triazole mononitrate; mp. 110.5° C.;
1-[2-(4-chlorophenyl)-2-(hexyloxy)ethyl]-1H-1,2,4-triazole mononitrate; mp. 117.6° C.; and
1-[2-(4-chlorophenyl)-2-(heptyloxy)ethyl]-1H-1,2,4-triazole mononitrate; mp. 118.3° C.

EXAMPLE XXXVI

A mixture of 5.2 parts of α-(2,4-dichlorophenyl)-1H-1,2,4-triazole-1-ethanol, 50 parts of dimethyl sulfoxide and 45 parts of benzene is stirred till all solid enters solution. Then there is added 1 part of a sodium hydride dispersion 78% and stirring is continued till gasevolution has ceased. After stirring for one hour at 40°-50° C., there are added 2.3 parts of 3-chloro-1-propyne. The whole is stirred overnight at room temperature. The reaction mixture is poured onto ice-water and the product is extracted with 1,1'-oxybisethane. The extract is washed with water, dried, filtered and evaporated. The oily residue is purified by column-chromatography over silica gel using a mixture of trichloromethane and methanol (95:5 by volume) as eluent. The pure fractions are collected and the eluent is evaporated. Upon standing overnight at room temperature, the residue solidifies. The product is filtered off and crystallized from 2,2'-oxybispropane, yielding 2 parts (33.8%) of 1-[2-(2,4-dichlorophenyl)-2-(2-propynyloxy)ethyl]-1H-1,2,4-triazole; mp. 84° C.

EXAMPLE XXXVII

A mixture of 5.2 parts of α-(2,4-dichlorophenyl)-1H-1,2,4-triazole-1-ethanol, 50 parts of dimethyl sulfoxide and 45 parts of benzene is stirred till all solid enters solution. Then there is added one part of a sodium hydride dispersion 78%. After foaming has ceased, stirring is continued for one hour at 40°-50° C. 3.8 Parts of dimethyl sulfate are added and the whole is stirred overnight at room temperature. The reaction mixture is poured onto ice-water and the product is extracted with 1,1'-oxybisethane. The extract is washed with water, dried, filtered and evaporated. The oily residue is purified by column-chromatography over silica gel using a mixture of trichloromethane and methanol (95:5 by volume) as eluent. The pure fractions are collected and the eluent is evaporated. The oily residue is converted into the nitrate salt in 2,2'-oxybispropane. The salt is filtered off and crystallized from a mixture of 2-propanol and 2,2'-oxybispropane, yielding 3 parts (44.7%) of 1-[2-(2,4-dichlorophenyl)-2-methoxyethyl]-1H-1,2,4-triazole nitrate; mp. 145.7° C.

EXAMPLE XXXVIII

A mixture of 3.2 parts of α-(2,4-dichlorophenyl)-1H-1,2,4-triazole-1-ethanol nitrate, 2.4 parts of 1-chloro-2-(chloromethyl)benzene, 1.5 parts of a sodium hydride dispersion 50%, 70 parts of dimethyl sulfoxide and 63 parts of benzene is stirred for 2.50 hours at room temperature. Water is added and the product is extracted twice with 2,2'-oxybispropane. The extract is washed twice with water and the solvent is removed in vacuo. The residue is crystallized from 2,2'-oxybispropane, yielding 3 parts of 1-{2-[(2-chlorophenyl)methoxy]-2-(2,4-dichlorophenyl)ethyl}-1H-1,2,4-triazole; mp. 106.4° C.

EXAMPLE XXXIX

Following the procedure of Example XXXVIII and using equivalent amounts of the appropriate starting materials, the following compounds are prepared in free base form or in the form of a nitrate salt after treatment of the free base with nitric acid.

1-{2-[(4-chlorophenyl)methoxy]-2-(2,4-dichlorophenyl)ethyl}-1H-1,2,4-triazole mononitrate; mp. 164.9° C.;
1-{2-(2,4-dichlorophenyl)-2-[(2,4-dichlorophenyl)methoxy]ethyl}-1H-1,2,4-triazole mononitrate; mp. 170° C.; and
1-{2-(2,4-dichlorophenyl)-2-[(2,6-dichlorophenyl)methoxy]ethyl}-1H-1,2,4-triazole; mp. 126.3° C.

EXAMPLE XL

Following the procedure of Example X there is prepared methyl 2,4-dibromobenzeneacetate; bp. 105°-110° C. at 0.1 mm. pressure, starting from 2,4-dibromobenzeneacetonitrile.

EXAMPLE XLI

Following the procedure of Example XIII and using equivalent amounts of the appropriate starting materials the following compounds are prepared:
2,4-dibromo-β-(2-methylpropyl)benzeneethanol as a residue;
2,4-dibromo-β-(1-methylethyl)benzeneethanol as a residue; and
2,4-dibromo-β-(1-methylpropyl)benzeneethanol as a residue.

EXAMPLE XLII

Following the procedure of Example XVI and using equivalent amounts of the appropriate starting materials there are prepared:
[2-(2,4-dibromophenyl)-4-methylpentyl]methanesulfonate as a residue;
[2-(2,4-dibromophenyl)-3-methylbutyl]methanesulfonate as a residue; and
[2-(2,4-dibromophenyl)-3-methylpentyl]methanesulfonate as a residue.

EXAMPLE XLIII

Following the procedure of Example XXXII there are prepared:
1-[2-(4-chlorophenyl)-2-(2-methylpropoxy)ethyl]-1H-1,2,4-triazole mononitrate; mp. 114.5° C.; and
1-[2-(2,4-dichlorophenyl)-2-(2-methylpropoxy)ethyl]-1H-1,2,4-triazole mononitrate; mp. 148° C.
by the reaction of (2-methylpropyl)methanesulfonate with respectively α-(4-chlorophenyl)-1H-1,2,4-triazole-1-ethanol and α-(2,4-dichlorophenyl)-1H-1,2,4-triazole-1-ethanol.

EXAMPLE XLIV

Following the procedure of Example XXXIV there is prepared 1-[2-(4-chlorophenyl)-2-(2-propenyloxy)ethyl]-1H-1,2,4-triazole mononitrate; mp. 100.4° C., by the reaction of α-(4-chlorophenyl)-1H-1,2,4-triazole-1-ethanol with 3-bromo-1-propene.

EXAMPLE XLV

Following the procedure of Example XXII and using equivalent amounts of the appropriate starting materials the following compounds are obtained:
1-[2-(2,4-dibromophenyl)-4-methylpentyl]-1H-1,2,4-triazole mononitrate; mp. 153.6° C.;
1-[2-(2,4-dibromophenyl)-3-methylbutyl]-1H-1,2,4-triazole mononitrate; mp. 142.9° C.;
1-[2-(4-chlorophenyl)-2-(1-methylethoxy)ethyl]-1H-1,2,4-triazole mononitrate; mp. 135.3° C.;
1-[2-(2,4-dichlorophenyl)-2-(1-methylethoxy)ethyl]-1H-1,2,4-triazole mononitrate; mp. 146.1° C.; and
1-[2-(2,4-dibromophenyl)-3-methylpentyl]-1H-1,2,4-triazole mononitrate; mp. 131.8° C.

We claim:

1. A chemical compound selected from the group consisting of a 1H-1,2,4-triazole derivative having the formula:

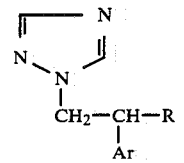

and the physiologically acceptable acid addition salts thereof, wherein:
Ar is a member selected from the group consisting of mono-, di- and tri-halophenyl and
R is a member selected from the group consisting of alkyl having from 1 to 10 carbon atoms, cycloalkyl, cycloalkyl-lower alkyl, lower alkenyl, aryl-lower alkyl, and aryloxy-lower alkyl said aryl being selected from the group consisting of phenyl, and substituted phenyl, wherein said substituted phenyl is phenyl having from 1 to 3 substituents independently selected from the group consisting of halo, lower alkyl, lower alkyloxy, cyano, nitro and phenyl provided that when more than 1 substituents are present only 1 thereof may be selected from the group consisting of cyano, nitro and phenyl.

2. A chemical compound selected from the group consisting of 1-[2-(2,4-dichlorophenyl)-3-methylbutyl]-1H-1,2,4-triazole and the physiologically acceptable acid addition salts thereof.

3. A chemical compound selected from the group consisting of 1-[2-(2,4-dichlorophenyl)-3-methylpentyl]-1H-1,2,4-triazole and the physiologically acceptable acid addition salts thereof.

4. A chemical compound selected from the group consisting of 1-[2-(2,4-dichlorophenyl)-4-methylpentyl]-1H-1,2,4-triazole and the physiologically acceptable acid addition salts thereof.

5. A chemical compound selected from the group consisting of 1-[2-(2,4-dichlorophenyl)hexyl]-1H-1,2,4-triazole and the physiologically acceptable acid addition salts thereof.

6. A chemical compound selected from the group consisting of 1-[4-(4-chlorophenyl)-2-(4-methylphenyl)butyl]-1H-1,2,4-triazole and the physiologically acceptable acid addition salts thereof.

7. A chemical compound selected from the group consisting of 1-[4-(4-chlorophenyl)-2-(4-fluorophenyl)butyl]-1H-1,2,4-triazole and the physiologically acceptable acid addition salts thereof.

8. A chemical compound selected from the group consisting of 1-[2-(2,4-dibromophenyl)hexyl]-1H-1,2,4-triazole and the physiologically acceptable acid addition salts thereof.

9. A chemical compound selected from the group consisting of 1-[2-(4-fluorophenyl)-4-(4-methylphenyl)butyl]-1H-1,2,4-triazole and the physiologically acceptable acid addition salts thereof.

10. A chemical compound selected from the group consisting of 1-[2-(2,4-dichlorophenyl)heptyl]-1H-1,2,4- triazole and the physiologically acceptable acid addition salts thereof.

11. A chemical compound selected from the group consisting of 1-[2-cyclohexyl-2-(2,4-dichlorophenyl)ethyl]-1H-1,2,4-triazole and the physiologically acceptable acid addition salts thereof.

12. A chemical compound selected from the group consisting of a 1H-1,2,4-triazole derivative having the formula

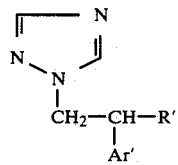

and the physiologically acceptable acid addition salts thereof, wherein:

Ar' is selected from the group consisting of dichlorophenyl and dibromophenyl; and R' is selected from the group consisting of alkyl having from 1 to 8 carbon atoms, cycloalkyl and 2-propenyl.

13. A composition for combatting fungi, comprising an inert carrier material and as an active ingredient an effective antifungal amount of a compound selected from the group consisting of a 1H-1,2,4-triazole derivative having the formula:

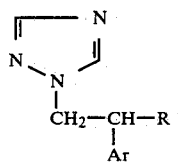

and the physiologically acceptable acid addition salts thereof, wherein:

Ar is a member selected from the group consisting of mono-, di- and tri-halophenyl and R is a member selected from the group consisting of alkyl having from 1 to 10 carbon atoms, cycloalkyl, cycloalkyl-lower alkyl, lower alkenyl, aryl-lower alkyl, and aryloxy-lower alkyl, said aryl being selected from the group consisting of phenyl, and substituted phenyl, wherein said substituted phenyl is phenyl having from 1 to 3 substituents independently selected from the group consisting of halo, lower alkyl, lower alkyloxy, cyano, nitro and phenyl provided that when more than 1 substituents are present only 1 thereof may be selected from the group consisting of cyano, nitro and phenyl.

14. A composition for combatting fungi, comprising an inert carrier material and as an active ingredient an effective antifungal amount of 1-[2-(2,4-dichlorophenyl)-3-methylbutyl]-1H-1,2,4-triazole and the physiologically acceptable acid addition salts thereof.

15. A composition for combatting fungi, comprising an inert carrier material and as an active ingredient an effective antifungal amount of 1-[2-(2,4-dichlorophenyl)hexyl]-1H-1,2,4-triazole and the physiologically acceptable acid addition salts thereof.

16. A composition for combatting fungi, comprising an inert carrier material and as an active ingredient an effective antifungal amount of 1-[2-cyclohexyl-2-(2,4-dichlorophenyl)ethyl]-1H-1,2,4-triazole and the physiologically acceptable acid addition salts thereof.

17. A chemical compound selected from the group consisting of 1-[2-(2,4-dichlorophenyl)pentyl]-1H-1,2,4-triazole and the physiologically acceptable acid addition salts thereof.

18. A chemical compound selected from the group consisting of a 1H-1,2,4-triazole derivative having the formula:

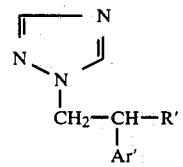

and the physiologically-acceptable acid addition salts thereof, wherein:

Ar' is selected from the group consisting of, mono- and di-halophenyl; and

R' is selected from the group consisting of alkyl having from 1 to 10 carbon atoms, cycloalkyl, loweralkenyl, arylmethyl, and arylethyl, wherein said aryl is phenyl, halophenyl, methylphenyl, or methoxyphenyl.

19. A chemical compound selected from the group consisting of a 1H-1,2,4-triazole derivative having the formula:

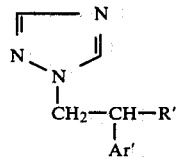

and the physiologically-acceptable acid addition salts thereof, wherein:

Ar' is, chlorophenyl, fluorophenyl, bromophenyl, dichlorophenyl, or dibromophenyl; and R' is alkyl having from 1 to 8 carbon atoms, cycloalkyl, or 2-propenyl.

20. A chemical compound selected from the group consisting of:
1-[2-(2,4-dichlorophenyl)butyl]-1H-1,2,4-triazole;
1-[2-(2,4-dichlorophenyl)pentyl]-1H-1,2,4-triazole;
1-[2-(2,4-dibromophenyl)hexyl]-1H-1,2,4-triazole;
1-[2-(2,4-dichlorophenyl)-3-methylpentyl]-1H-1,2,4-triazole;
1[2-(2,4-dichlorophenyl)-4-methylpentyl]-1H-1,2,4-triazole;
1-[2-(2,4-dichlorophenyl)heptyl]-1H-1,2,4-triazole;
1-[2-(2,4-dichlorophenyl)decyl]-1H-1,2,4-triazole;
1-[2-cyclopentyl-2-(2,4-dichlorophenyl)ethyl]-1H-1,2,4-triazole;
1-[2-cyclohexyl-2-(2,4-dichlorophenyl)ethyl]-1H-1,2,4-triazole;
1-[3-cyclohexyl-2-(2,4-dichlorophenyl)propyl]-1H-1,2,4-triazole;
1-[4-cyclohexyl-2-(2,4-dichlorophenyl)butyl]-1H-1,2,4-triazole;
1-[2-(2,4-dichlorophenyl)-4-pentenyl]-1H-1,2,4-triazole; and
1-[2-(2,4-dichlorophenyl)-5-hexenyl]-1H-1,2,4-triazole; and the pharmaceutically acceptable acid addition salts thereof.

21. A composition for combatting fungi, comprising an inert carrier material and as an active ingredient an effective anti-fungal amount of 1-[2-(2,4-dichlorophenyl)pentyl]-1H-1,2,4-triazole or a physiologically acceptable acid addition salt thereof.

22. A method of combatting fungal growth on plants which comprises treating said plants with an effective fungal combatting amount of a chemical compound selected from the group consisting of a 1H-1,2,4-triazole derivative having the formula:

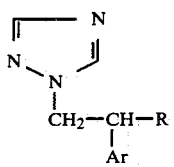

and the physiologically acceptable acid addition salts thereof, wherein:

Ar is a member selected from the group consisting of mono-, di- and tri-halophenyl; and R is alkyl having from 1 to 10 carbon atoms, cycloalkyl, cycloalkyl-lower alkyl, lower alkenyl, aryl-lower alkyl or, aryloxy-lower alkyl, said aryl being selected from the group consisting of phenyl and substituted phenyl, wherein said substituted phenyl is phenyl having from 1 to 3 substituents independently selected from the group conssisting of halo, lower alkyl, lower alkyloxy, cyano, nitro and phenyl provided that when more than 1 substituents are present only 1 thereof may be selected from the group consisting of cyano, nitro and phenyl.

23. A method of combatting fungal growth on plants which comprises treating said plants with an effective fungal combatting amount of a chemical compound selected from the group consisting of 1-[2-(2,4-dichlorophenyl)-3-methylbutyl]-1H-1,2,4-triazole and the physiologically acceptable acid addition salts thereof.

24. A method of combatting fungal growth on plants which comprises treating said plants with an effective fungal combatting amount of a chemical compound selected from the group consisting of 1-[2-(2,4-dichlorophenyl)-3-methylpentyl]-1H-1,2,4-triazole and the physiologically acceptable acid addition salts thereof.

25. A method of combatting fungal growth on plants which comprises treating said plants with an effective fungal combatting amount of a chemical compound selected from the group consisting of 1-[2-(2,4-dichlorophenyl)-4-methylpentyl]-1H-1,2,4-triazole and the physiologically acceptable acid addition salts thereof.

26. A method of combatting fungal growth on plants which comprises treating said plants with an effective fungal combatting amount of a chemical compound selected from the group consisting of 1-[2-(2,4-dichlorophenyl)hexyl]-1H-1,2,4-triazole and the physiologically acceptable acid addition salts thereof.

27. A method of combatting fungal growth on plants which comprises treating said plants with an effective fungal combatting amount of a chemical compound selected from the group consisting of 1-[4-(4-chlorophenyl)-2-(4-methylphenyl)butyl]-1H-1,2,4-triazole and the physiologically acceptable acid addition salts thereof.

28. A method of combatting fungal growth on plants which comprises treating said plants with an effective fungal combatting amount of a chemical compound selected from the group consisting of 1-[4-(4-chlorophenyl)-2-(4-fluorophenyl)butyl]-1H-1,2,4-triazole and the physiologically acceptable acid addition salts thereof.

29. A method of combatting fungal growth on plants which comprises treating said plants with an effective fungal combatting amount of a chemical compound selected from the group consisting of 1-[2-(2,4-dibromophenyl)hexyl]-1H-1,2,4-triazole and the physiologically acceptable acid addition salts thereof.

30. A method of combatting fungal growth on plants which comprises treating said plants with an effective fungal combatting amount of a chemical compound selected from the group consisting of 1-[2-(4-fluorophenyl)-4-(4-methylphenyl)butyl]-1H-1,2,4-triazole and the physiologically acceptable acid addition salts thereof.

31. A method of combatting fungal growth on plants which comprises treating said plants with an effective fungal combatting amount of a chemical compound selected from the group consisting of 1-[2-(2,4-dichlorophenyl)heptyl]-1H-1,2,4-triazole and the physiologically acceptable acid addition salts thereof.

32. A method of combatting fungal growth on plants which comprises treating said plants with an effective fungal combatting amount of a chemical compound selected from the group consisting of 1-[2-cyclohexyl-2-(2,4-dichlorophenyl)ethyl]-1H-1,2,4-triazole and the physiologically acceptable acid addition salts thereof.

33. A method of combatting fungal growth on plants which comprises treating said plants with an effective fungal combatting amount of a chemical compound selected from the group consisting of a 1H-1,2,4-triazole derivative having the formula:

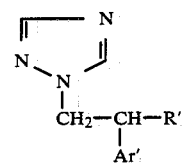

and the physiologically acceptable acid addition salts thereof, wherein:

Ar' is selected from the group consisting of dichlorophenyl and dibromophenyl; and R' is selected from the group consisting of alkyl having from 1 to 8 carbon atoms, cycloalkyl and 2-propenyl.

34. A method of combatting fungal growth on plants which comprises treating said plants with an effective fungal combatting amount of a chemical compound selected from the group consisting of 1-[2-(2,4-dichlorophenyl)pentyl]-1H-1,2,4-triazole and the physiologically acceptable acid addition salts thereof.

35. A method of combatting fungal growth on plants which comprises treating said plants with an effective fungal combatting amount of a chemical compound selected from the group consisting of 1H-1,2,4-triazole derivative having the formula:

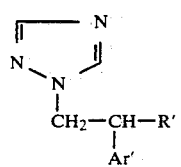

and the physiologically-acceptable acid addition salts thereof, wherein:
Ar' is selected from the group consisting of, mono- and di-halophenyl; and
R' is selected from the group consisting of alkyl having from 1 to 10 carbon atoms, cycloalkyl, loweralkenyl, arylmethyl, and arylethyl, wherein said aryl is phenyl, halophenyl, methylphenyl, or methoxyphenyl.

36. A method of combatting fungal growth on plants which comprises treating said plants with an effective fungal combatting amount of a chemical compound selected from the group consisting of a 1H-1,2,4-triazole derivative having the formula:

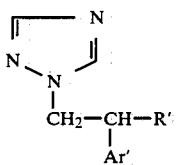

and the physiologically-acceptable acid addition salts thereof, wherein:
Ar' is, chlorophenyl, fluorophenyl, bromophenyl, dichlorophenyl, or dibromophenyl; and
R' is alkyl having from 1 to 8 carbon atoms, cycloalkyl, or 2-propenyl.

37. A method of combatting fungal growth on plants which comprises treating said plants with an effective fungal combatting amount of a chemical compound selected from the group consisting of:
1-[2-(2,4-dichlorophenyl)butyl]-1H-1,2,4-triazole;
1-[2-(2,4-dichlorophenyl)pentyl]-1H-1,2,4-triazole;
1-[2-(2,4-dibromophenyl)hexyl]-1H-1,2,4-triazole;
1-[2-(2,4-dichlorophenyl)-3-methylpentyl]-1H1,2,4-triazole;
1-[2-(2,4-dichlorophenyl)-4-methylpentyl]-1H-1,2,4-triazole;
1-[2-(2,4-dichlorophenyl)heptyl]-1H-1,2,4-triazole;
1-[2-(2,4-dichlorophenyl)decyl]-1H-1,2,4-triazole;
1-[2-cyclopentyl-2-(2,4-dichlorophenyl)ethyl]-1H-1,2,4-triazole;
1-[2-cyclohexyl-2-(2,4-dichlorophenyl)ethyl]-1H-1,2,4-triazole;
1-[3-cyclohexyl-2-(2,4-dichlorophenyl)propyl]-1H-1,2,4-triazole;
1-[4-cyclohexyl-2-(2,4-dichlorophenyl)butyl]-1H-1,2,4-triazole;
1-[2-(2,4-dichlorophenyl)-4-pentenyl]-1H-1,2,4-triazole; and
1-[2-(2,4-dichlorophenyl)-5-hexenyl]-1H-1,2,4-triazole; and
the pharmaceutically acceptable acid addition salts thereof.

38. A chemical compound selected from the group consisting of 1-[2-(2,4-dichlorophenyl)butyl]-1H-1,2,4-triazole and the physiologically acceptable acid addition salts thereof.

39. A chemical compound selected from the group consisting of 1-[2-cyclopentyl-2-(2,4-dichlorophenyl)ethyl]-1H-1,2,4-triazole and the physiologically acceptable acid addition salts thereof.

40. A chemical compound selected from the group consisting of 1-[2-(2,4-dichlorophenyl)-4-pentenyl]-1H-1,2,4-triazole and the physiologically acceptable acid addition salts thereof.

41. A chemical compound selected from the group consisting of 1-[2-(2,4-dichlorophenyl)-5-hexenyl]-1H-1,2,4-triazole and the physiologically acceptable acid addition salts thereof.

42. A chemical compound selected from the group consisting of 1-[2-(2,4-dichlorophenyl)propyl]-1H-1,2,4-triazole and the physiologically acceptable acid addition salts thereof.

43. A chemical compound selected from the group consisting of 1-[4-(4-bromophenyl)-2-(2-chlorophenyl)butyl]-1H-1,2,4-triazole and the physiologically acceptable acid addition salts thereof.

* * * * *

Notice of Adverse Decisions in Interference

In Interference No. 102,074, involving Patent No. 4,598,085, J. Heeres, L. J. J. Backx, J. A. Mostmans, FUNGICIDAL 1-(2-ARYL-2-R-ETHYL)-1H-1, 2, 4-TRIAZOLES, final judgment adverse to the patentees was rendered July 18, 1991, as to claim 1-43.

*(Official Gazette December 24, 1991).*